United States Patent
Cai et al.

(10) Patent No.: US 9,777,452 B2
(45) Date of Patent: Oct. 3, 2017

(54) GRAVITY TYPE PORE PRESSURE DYNAMIC PENETRATION DEVICE FOR SHALLOW LAYER SEABED SOIL

(71) Applicant: SOUTHEAST UNIVERSITY, Nanjing (CN)

(72) Inventors: Guojun Cai, Nanjing (CN); Jun Lin, Nanjing (CN); Gongqiao Geng, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 0 days.

(21) Appl. No.: 15/503,399

(22) PCT Filed: Mar. 23, 2015

(86) PCT No.: PCT/CN2015/074823
§ 371 (c)(1),
(2) Date: Feb. 12, 2017

(87) PCT Pub. No.: WO2016/023365
PCT Pub. Date: Feb. 18, 2016

(65) Prior Publication Data
US 2017/0233968 A1 Aug. 17, 2017

(30) Foreign Application Priority Data
Aug. 12, 2014 (CN) .......................... 2014 1 0396532

(51) Int. Cl.
E21C 39/00 (2006.01)
E02D 1/02 (2006.01)
G01L 23/26 (2006.01)

(52) U.S. Cl.
CPC .............. *E02D 1/027* (2013.01); *G01L 23/26* (2013.01)

(58) Field of Classification Search
None
See application file for complete search history.

(56) References Cited

U.S. PATENT DOCUMENTS 5,259,240 A * 11/1993 Raines .................... E02D 1/025
73/84
6,208,940 B1 3/2001 Kram et al.
(Continued)

FOREIGN PATENT DOCUMENTS

CN 101858075 A 10/2010
CN 102174808 A 9/2011
(Continued)

*Primary Examiner* — Andre Allen
(74) *Attorney, Agent, or Firm* — Gokalp Bayramoglu

(57) ABSTRACT

A gravity-type pore pressure dynamic penetration device for exploration of shallow-layer seabed soil includes a third drop hammer, a second drop hammer, a first drop hammer, a stable empennage, and a probe rod which are sequentially arranged from top to bottom. A sidewall friction sleeve is arranged outside a probe rod lower cylinder. A friction sleeve sensor is provided on an inner sidewall of the sidewall friction sleeve. A first pore water pressure sensor, a conical tip pressure sensor, a temperature compensation sensor, and an inclinometer sensor are provided in the middle of the probe rod lower cylinder. A second pore water pressure sensor and an acceleration sensor are provided in the middle of a probe rod upper cylinder. The tail portion of the probe rod, that is, the upper portion of the probe rod upper cylinder is connected to the stable empennage.

2 Claims, 1 Drawing Sheet

(56) References Cited

U.S. PATENT DOCUMENTS

2006/0107772 A1* 5/2006 Shinn, II ................ G01N 33/24
                                                    73/864.43
2010/0024535 A1* 2/2010 Maeda ...................... E02D 1/02
                                                    73/84

FOREIGN PATENT DOCUMENTS

| CN | 102518107 A | 6/2012 |
| CN | 104164860 A | 11/2014 |
| GB | 2185324 A | 7/1987 |

* cited by examiner

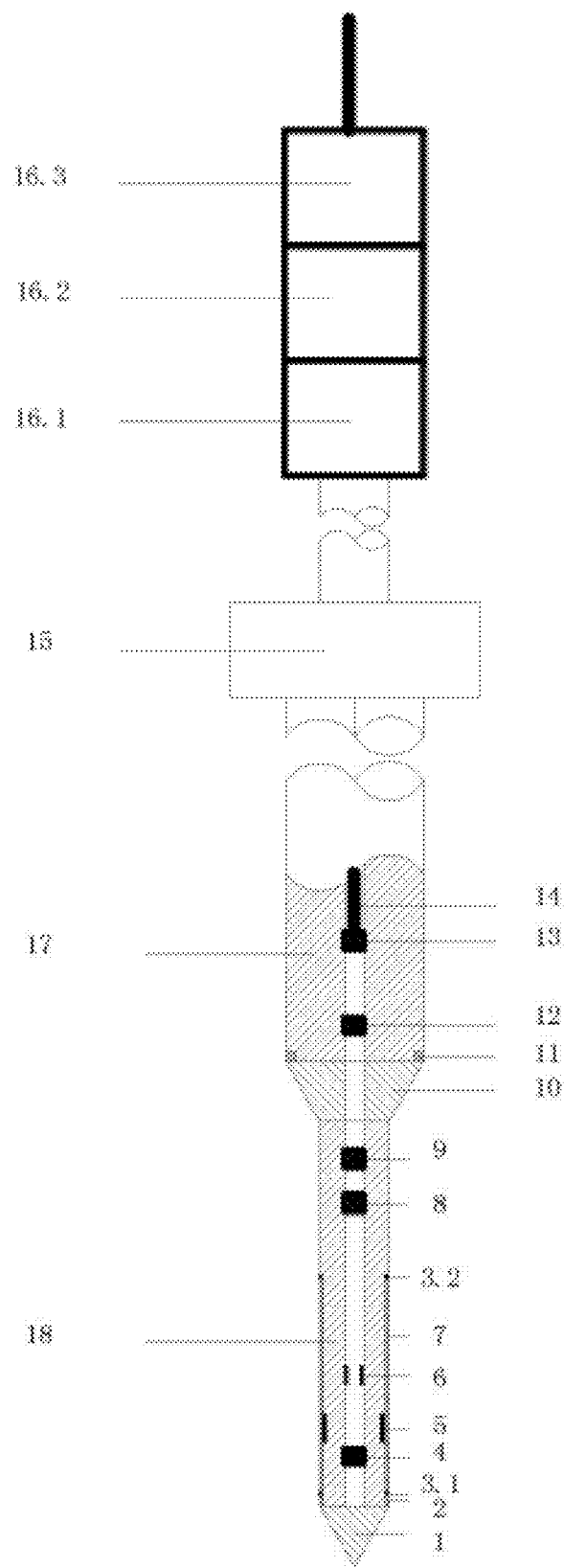

GRAVITY TYPE PORE PRESSURE DYNAMIC PENETRATION DEVICE FOR SHALLOW LAYER SEABED SOIL

CROSS REFERENCE TO RELATED APPLICATIONS

This application is the national phase of International Application No. PCT/CN2015/074823, filed on Mar. 23, 2015, which is based upon and claims priority to Chinese Patent Application No. 201410396532.1, filed on Aug. 12, 2014, the entire contents of which are incorporated herein by reference.

TECHNICAL FIELD OF THE INVENTION

The present invention relates to a gravity-type pore pressure dynamic penetration device for exploration of shallow-layer seabed soil, which belongs to a dynamic penetration device in the field of in-situ testing in marine geotechnical engineering.

BACKGROUND OF THE INVENTION

The engineering properties of seabed soil, such as undrained shear strength, compression index, and coefficient of permeability are influenced by many factors including gain composition, unit weight, and effective stress history of seabed soil as well as pore water pressure of in-situ soil. The engineering properties of seabed soil are generally related to in-situ stress history and pore water pressure of soil. In conventional marine exploration, due to stress disturbance, it is hard to acquire pore water pressure and in-situ stress history of seabed soil through conventional drill hole sampling, and the measured physico-mechanical property indexes of seabed soil usually cannot represent original state indicators of soil layers, thereby greatly reducing the engineering application value of soil parameters.

The present invention provides an in-situ pore pressure dynamic penetration device applicable to shallow-layer seabed soil of various depths, which can accurately acquire in-situ testing parameters of shallow-layer seabed soil, measure soil parameters after soil disturbance, comprehensively and accurately learn about the engineering properties of shallow-layer seabed soil, effectively reduce the evaluation period of engineering geological exploration of seabed soil, and reduce the cost of marine engineering exploration.

SUMMARY OF THE INVENTION

Technical Problem

The technical problem to be solved by the present invention is to develop a gravity-type in-situ pore pressure dynamic penetration, device applicable to shallow-layer seabed soil of various depths, in the case that there is so far no marine exploration device for in-situ testing capable of rapidly evaluating mechanical properties of shallow-layer seabed soil domestically.

Technical Solution

A gravity-type pore pressure dynamic penetration device for shallow-layer seabed soil according to the present invention includes a third drop hammer, a second drop hammer, a first drop hammer, a stable empennage, and a probe rod which are sequentially arranged from top to bottom. The probe rod includes a probe rod upper cylinder, a central reamer, and a probe rod lower cylinder which are sequentially arranged from top to bottom. A conical tip is provided on the bottom end of the probe rod. A first pore pressure filter ring is provided between the conical tip and the probe rod lower cylinder. A second pore pressure filter ring is provided between the probe rod upper cylinder and the central reamer. A sidewall friction sleeve is arranged outside the probe rod lower cylinder. A first seal ring and a second seal ring are provided on the upper and lower ends of the sidewall friction sleeve respectively. A friction sleeve sensor is provided on an inner sidewall of the sidewall friction sleeve. A pore water pressure sensor, a conical tip pressure sensor, a temperature compensation sensor, and an inclinometer sensor are provided in the middle of the probe rod lower cylinder. A pore water pressure sensor and an acceleration sensor are provided in the middle of the probe rod upper cylinder. The tail portion of the probe rod, that is, the upper portion of the probe rod upper cylinder is connected to the stable empennage. The stable empennage is connected to the first drop hammer, the second drop hammer, and the third drop hammer with automatic drop triggering means. Signal transmission of the whole dynamic penetration device is realized by connecting the above parts with a coaxial cable.

The third drop hammer, the second drop hammer, and the first drop hammer are the same, and each have an outer diameter less than that of the reamer.

Advantageous Effect

The present invention solves the problem that there is no marine in-situ pore pressure dynamic penetration device applicable to various depths domestically, whereby in-situ testing parameters of shallow-layer seabed soil of different depths can be rapidly and accurately acquired, the impacts from weather and ocean waves are small, the marine exploration periods of deep-layer and shallow-layer soil can be effectively reduced, and the exploration cost is lowered.

BRIEF DESCRIPTION OF THE DRAWINGS

FIG. 1 is a general schematic view of a device according to the present invention, including:

conical tip 1, first pore pressure filter ring 2, first seal ring 3.1, second seal ring 3.2, first pore water pressure sensor 4, friction sleeve sensor 5, conical tip pressure sensor 6, sidewall friction sleeve 7, inclinometer sensor 8, temperature compensation sensor 9, central reamer 10, second pore pressure filter ring 11, second pore water pressure sensor 12, acceleration sensor 13, coaxial cable 14, stable empennage 15, first drop hammer 16.1, second drop hammer 16.2, and third drop hammer 16.3 with automatic drop triggering means, probe rod upper cylinder 17, probe rod lower cylinder 18.

DETAILED DESCRIPTION OF THE INVENTION

The present invention is further described below with reference to embodiments and the accompanying drawings.

A gravity-type pore pressure dynamic penetration device of the present invention includes a third drop hammer 16.3, a second drop hammer 16.2, a first drop hammer 16.1, a stable empennage 15, and a probe rod which are sequentially arranged from top to bottom. The probe rod includes a probe rod upper cylinder 17, a central reamer 10, and a probe rod lower cylinder 18 which are sequentially arranged from top to bottom. A conical tip 1 is provided on the bottom end of the probe rod. A first pore pressure filter ring 2 is provided between the conical tip 1 and the probe rod lower cylinder 18. A second pore pressure filter ring 11 is provided between the probe rod upper cylinder 17 and the central reamer 10. A sidewall friction sleeve 7 is arranged outside the probe rod lower cylinder 18. A first seal ring 3.1 and a second seal ring 3.2 are provided on the upper and lower ends of the sidewall friction sleeve 7 respectively. A fiction sleeve sensor 5 is provided on an inner sidewall of the sidewall friction sleeve 7. A pore water pressure sensor 4, a conical tip pressure sensor 6, a temperature compensation sensor 8, and an inclinometer sensor 9 are provided in the middle of the probe rod lower cylinder 18. A pore water pressure sensor 12 and an acceleration sensor 13 are provided in the middle of the probe rod upper cylinder 17. The tail portion of the probe rod, that is, the upper portion of the probe rod upper cylinder 17 is connected to the stable empennage 15. The stable empennage 15 is connected to the first drop hammer 16.1, the second drop hammer 16.2, and the third drop hammer 16.3 with automatic drop triggering means. Signal transmission of the whole dynamic penetration device is realized by connecting the above parts with a coaxial cable 14.

The two pore pressure filter rings have a thickness of 5 mm.

The pore water pressure sensor has a maximum measurement range of 3 MPa and a resolution of 100 Pa.

The acceleration sensor has a sensitivity of 50 pc/g and an impact threshold of 5000 g.

The reamer is a circular truncated cone body having a taper angle of 60°, an upper diameter of 72 mm, and a lower diameter of 36 mm.

The stable empennage is of a cross-plate type, and each fin has a height of 50 mm and a width of 40 mm.

The drop hammers each have a weight of 14 kg, a drop distance of 100 mm, and an outer diameter of 60 mm.

When a predetermined exploration location is reached, the gravity-type pore pressure dynamic penetration device is entirely immersed in seawater for more than five minutes such that the first pore pressure filter ring 2 and the second pore pressure filter ring 11 reach a saturated state, and the first drop hammer 16.1, the second drop hammer 16.2, and the third drop hammer 16.3 are fixed. The pore pressure dynamic penetration device is pulled by a steel wire rope to drop freely to the bottom of the sea at a speed of 2 m/s. During the penetration of the pore pressure dynamic penetration device into seabed soil, the resistance against the conical tip 1, the pore water pressure on the first pore pressure filter ring 2 and the second pore pressure filter ring 11, the friction against the sidewall friction sleeve 7, the inclination of the inclinometer sensor 8, and the acceleration of the acceleration sensor 13 can be measured. When the penetration of the device stops, a pore pressure dissipation test is carried out, and the pore pressure dissipation time $T_{50}$ of the first pore pressure filter ring 2 and the second pore pressure filter ring 11 respectively can be measured. After the pore pressure dissipation test ends, the first drop hammer 16.1 is triggered to drop freely, the pore pressure dynamic penetration device keeps penetration under the hammering, and the resistance against the conical tip 1, the pore water pressure on the first pore pressure filter ring 2. and the second pore pressure filter ring 11, the friction against the sidewall friction sleeve 7, the inclination of the inclinometer sensor 8, and the acceleration of the acceleration sensor 13 are continuously recorded during the penetration process. When the penetration of the device stops, the pore pressure dissipation time $T_{50}$ of soil can be measured. The second drop hammer 16.2 and the third drop hammer 16.3 are sequentially triggered to repeat the above steps for the pore pressure dynamic penetration test.

During the penetration process, in the presence of the stable empennage 15, the pore pressure dynamic penetration device remains stable while the first chop hammer 16.1, the second drop hammer 16.2, and the third drop hammer 16.3 are at work.

The measured pore pressure dissipation time $T_{50}$ of the first pore pressure filter ring 2 is equivalent to dissipation data of in-situ soil. The measured pore pressure dissipation time $T_{50}$ of the second pore pressure filter ring 11 is dissipation data after disturbance from reaming of the central reamer 10.

The test data of the inclinometer sensor 8 and the acceleration sensor 13 can be subjected to numerical computation to obtain the final penetration depth. The test. data of the resistance against the conical tip 1, the pore water pressure on the first pore pressure filter ring 2 and the second pore pressure filter ring 11, the friction against the sidewall fiction sleeve 7, and the pore pressure dissipation time. $T_{50}$ of the first pore pressure filter ring 2 and the second pore pressure filter ring 11 can be used to evaluate the engineering properties of seabed soil in situ and after disturbance.

What is claimed is:

1. A gravity-type pore pressure dynamic penetration device for shallow-layer seabed soil, comprising:
    a first drop hammer;
    a second drop hammer;
    a third drop hammer;
    a stable empennage; and
    a probe rod;
    wherein the first drop hammer, the second drop hammer, the third drop hammer, the stable empennage, and the probe rod are sequentially arranged from top to bottom;
    wherein
    the probe rod comprises a probe rod upper cylinder, a central reamer, and a probe rod lower cylinder which are sequentially arranged from top to bottom;
    a conical tip is provided on a bottom end of the probe rod;
    a first pore pressure filter ring is provided between the conical tip and the probe rod lower cylinder;
    a second pore pressure filter ring is provided between the probe rod upper cylinder and the central reamer;
    a sidewall friction sleeve is arranged outside the probe rod lower cylinder;
    a first seal ring and a second seal ring are provided on an upper end and a lower end of the sidewall friction sleeve respectively;
    a friction sleeve sensor is provided on an inner sidewall of the sidewall friction sleeve;
    a first pore water pressure sensor, a conical tip pressure sensor, a temperature compensation sensor, and an inclinometer sensor are provided in the middle of the probe rod lower cylinder;
    a second pore water pressure sensor and an acceleration sensor are provided in the middle of the probe rod upper cylinder;
    a tail portion of the probe rod, that is, an upper portion of the probe rod upper cylinder is connected to the stable empennage;
    the stable empennage is connected to the first drop hammer, the second drop hammer, and the third drop hammer with automatic drop triggering device;
    signal transmission of whole dynamic penetration device is realized by a coaxial cable.

2. The gravity-type pore pressure dynamic penetration device for shallow-layer seabed soil according to claim 1, wherein the first drop hammer, the second drop hammer, and the third drop hammer are the same, and each of the first drop hammer, the second drop hammer, and the third drop hammer has an outer diameter less than that of the central reamer.

* * * * *